# United States Patent [19]

Panzera

[11] 4,455,383
[45] Jun. 19, 1984

[54] SINGLE-FRIT GLASS CERAMIC
[75] Inventor: Carlino Panzera, Belle Mead, N.J.
[73] Assignee: Johnson & Johnson Dental Products Company, East Windsor, N.J.
[21] Appl. No.: 482,076
[22] Filed: Apr. 4, 1983
[51] Int. Cl.$^3$ .............................................. C03C 3/22
[52] U.S. Cl. ......................................... 501/6; 106/35; 501/21
[58] Field of Search ....................... 501/6, 21; 106/35

[56] References Cited

U.S. PATENT DOCUMENTS 4,101,330  7/1978  Burk et al. ............................ 106/35

FOREIGN PATENT DOCUMENTS 48-31558  9/1973  Japan ..................................... 106/35
53-31716  3/1978  Japan ..................................... 106/35

OTHER PUBLICATIONS

Hoshikawa, Takeshi et al., "A New Leucite Glass-Ceramic Glaze: Mechanical Properties and Bonding to Gold-Alloy", Kagaku to Kogyo, Osaka (Science and Industry) 48(8), 1974, pp. 311-315.
Chem. Abstr. 94 (1981), Item 161261.
Hahn, C. et al., "Importance of the Glass Ceramic System Potassium Oxide-Aluminum Oxide-Silicon Dioxide in Dental Porcelain", Ber. Dtsch Keram. Ges. 1980, 57 (9-10), pp. 208-214 (Eng/Ger).

*Primary Examiner*—Helen M. McCarthy
*Attorney, Agent, or Firm*—Charles J. Metz

[57] ABSTRACT

There is disclosed a single-frit porcelain powder, suitable for use as a porcelain layer on metal-base dental restorations, and having a fired coefficient of thermal expansion within the range of from about 12 to about $14 \times 10^{-6}$ in./in. °C., wherein said single frit porcelain is of the following composition:

| Component | Weight Percent |
|---|---|
| $SiO_2$ | $65\frac{1}{2} \pm 4$ |
| $Al_2O_3$ | $15 \pm 2$ |
| $K_2O$ | $12\frac{1}{2} - 1, + 2$ |
| Flux | $4 \pm 1$ |
| MO | $2 \pm 1$ | wherein M represents calcium, magnesium, or a mixture thereof, and Flux represents sodium oxide or lithium oxide, or a mixture thereof, and, optionally, may also contain boron oxide.

3 Claims, No Drawings

SINGLE-FRIT GLASS CERAMIC

The invention relates to a single-frit glass ceramic material that is useful as a porcelain covering in metal-base dental restorations.

BACKGROUND OF THE INVENTION

Dental crown and bridge restorations are often made with a metal base having a jacket or covering of dental porcelain so that the restoration will closely resemble the natural tooth. Such restorations have been used for many years.

The type of porcelain that is most often employed today in such restorations is that described in the two Weinstein et al. patents, U.S. Pat. Nos. 3,052,982 and 3,052,983. The Weinstein et al. patents address the problem of preparing a porcelain whose coefficient of thermal expansion will match that of the metal base so that excessive stress formation will not occur during the production of the restoration.

The solution proposed by Weinstein et al. is to make a dental porcelain composed of two different frits, one having a high coefficient of expansion and the other having a much lower coefficient of expansion, to result in a porcelain having a coefficient of expansion intermediate between the two materials, and which will match the dental alloy employed as the base.

If one attempts to make a single frit ceramic material whose composition is the average of the two components employed in the two-frit mixture of the type contemplated by Weinstein et al., the resulting porcelain will have too low a coefficient of expansion, and cannot, therefore, be employed with metal-base dental restorations.

The present invention is based upon the discovery of a single frit glass-ceramic material that has a coefficient of expansion that will match that of the majority of metal alloys employed in producing dental restorations. The use of a single frit glass ceramic material reduces the criticality in mixing the components so as to obtain the desired coefficient of thermal expansion and fusion temperature. As a result, better control over the desired properties and/or composition can be obtained.

SUMMARY OF THE INVENTION

The invention provides a glass ceramic material composed of a single frit, whose composition is the following:

| Component | Weight Percent |
|---|---|
| $SiO_2$ | $65\frac{1}{4} \pm 4$ |
| $Al_2O_3$ | $15 \pm 2$ |
| $K_2O$ | $12\frac{1}{4} - 1, + 2$ |
| Flux[1] | $4 \pm 1$ |
| $MO$[2] | $2 \pm 1$ |

[1]Flux is $Na_2O$ and/or $Li_2O$, and, optionally, $B_2O_3$
[2]M is calcium or magnesium or a mixture of the two.

THE PRIOR ART

The Weinstein patents, cited above, are believed to be the most relevant prior art. A survey discussion of dental porcelain is found in Chapter 31 of the text "Science of Dental Materials", by Skinner and Phillips, 7th Edition, W. B. Saunders and Company (1973), pages 526–555.

DETAILED DESCRIPTION OF THE INVENTION

The general technique for the construction of a porcelain coated dental restoration (i.e., crown or bridge), is the following: first an impression is taken of the denture area that has been prepared to receive the restoration. A die is prepared from the impression, and a metal base (called the "coping")is cast to fit this die. The metal base has an internal shape to match exactly the prepared denture. A porcelain powder is then mixed with water to form a slurry, which is then applied to the metal base by standard procedures. The slurry is shaped in the form of the finished crown or multiple unit bridge. The porcelain is then dried, and fired in an electric furnace to the desired firing temperature. The crown or bridge may be fired several times before the final form is obtained, and the porcelain may be applied in several layers.

As can be seen from this summary, there is a significant temperature change from the firing temperature to room temperature, as the restoration is alternately cooled and fired. Therefore, significant stress can be induced in the restoration if the coefficient of thermal expansion of the porcelain coating does not closely match that of the metal base.

This invention provides a single-frit ceramic material that has a coefficient of expansion that closely matches that of a large proportion of the metal bases employed in making dental restorations.

The ceramic material of the invention has the following composition:

| Component | Weight Percent Broad | Weight Percent Preferred |
|---|---|---|
| $SiO_2$ | $65\frac{1}{4} \pm 4$ | $65\frac{1}{4} \pm 1$ |
| $Al_2O_3$ | $15 \pm 2$ | $15 \pm 1$ |
| $K_2O$ | $12\frac{1}{4} - 1, + 2$ | $12\frac{1}{4} \pm 1$ |
| Flux | $4 \pm 1$ | $4 \pm 1$ |
| MO | $2 \pm 1$ | $2 \pm \frac{1}{2}$ |

(As mentioned above, Flux=$Na_2O$ and/or $Li_2O$, and, optionally, $B_2O_3$, and M=Ca or Mg or mixture thereof.)

This porcelain material can be made by making a mixture of the powdered metal oxides, in the proportions mentioned above, or a mineral such as feldspar or nepheline syenite can be mixed with the appropriate metal oxides to make up the above-stated composition. (The alkali metal oxides and the alkaline earth metal oxides are most convenient to use in the form of their carbonates). In one preferred aspect, the flux is composed of $Na_2O$ in amounts of $2\frac{3}{4} \pm \frac{1}{4}$ weight percent, and $Li_2O$ in amounts of $1\frac{1}{4} \pm \frac{1}{4}$ weight percent. As is known in the art, boron oxide tends to lower the coefficient of thermal expansion. This should be taken into account if it is used, and correspondingly more sodium oxide may need to be used in the flux (sodium oxide tends to raise the coefficient of thermal expansion more than lithium oxide does).

The usual pigments, such as chromates, vanadates, and manganates can be added to the porcelain in small amounts, as well as opacifiers such as tin oxide, if desired.

The components are blended, preferably reduced to a very fine powder as by ball milling for 1 to 3 hours, and then fused to form a glass. The fusion can be carried out at 1300° C.±100° C. for from about 1 to 4 hours. After the fusion, the material is quenched in water, and then reheated to elevated temperature (e.g., 1000° C.±50° C.) for from about 1 to about 6 hours to permit the crystalline phase (i.e., leucite) to form and grow. After the desired amount of crystalline material has formed, the material is quenched, crushed, and reduced to a fine powder as by ball milling for from 1 to 3 hours. Preferably, the powder is fine enough to pass through a 160 to 170 mesh screen.

After the porcelain powder has been prepared, it is then employed in making a dental restoration in the conventional manner. The examples below illustrate certain aspects of the invention.

were heated at a 90° to 100° F. per minute heat-up rate to a temperature of 1800° F. The coefficients of thermal expansion of the specimens made from Examples 1 and 2 were measured in a dilatometer. They did not vary significantly after these 10 cycles. (The controls did not vary either.)

In Table II, Control 1 is a commercial material which consists of a mixture of (A) and (E) in proportions of about 50:50 (by weight). The experiment identified as "Control 2", is a single-frit porcelain whose composition is the same as the admixture of A plus E. As is noted, the coefficient of thermal expansion is only 10.3, which is not sufficient for use with most of the metal bases that are used in dental restorations.

TABLE II

|  | Control 1 | | | | | | |
|---|---|---|---|---|---|---|---|
|  | Conventional High Exp (A) | Conventional Glass (E) | Admixture of A & E | Control 2 | Control 3 | Example 1 | Example 2 |
| $SiO_2$ | 62.91 | 67.75 | 65.53 | 65.53 | 65.53 | 65.53 | 65.53 |
| $Al_2O_3$ | 18.46 | 11.21 | 14.88 | 14.88 | 14.88 | 14.88 | 14.88 |
| $K_2O$ | 13.04 | 7.08 | 10.00 | 10.00 | 11.00 | 12.00 | 13.00 |
| $Na_2O$ | 2.21 | 9.08 | 5.67 | 5.67 | 4.67 | 3.67 | 2.67 |
| $Li_2O$ | 2.49 | — | 1.25 | 1.25 | 1.25 | 1.25 | 1.25 |
| CaO | 0.08 | 2.50 | 1.29 | 1.29 | 1.29 | 1.29 | 1.29 |
| MgO | 0.02 | 1.60 | 0.81 | 0.81 | 0.81 | 0.81 | 0.81 |
|  | 99.21 | 99.22 | 99.43 | 99.43 | 99.43 | 99.43 | 99.43 |
| Coef. of T.E. ($\times 10^6$ in/in °C.) after 5 hrs. @ 1000° C.: | 18 | 8 | 13.5 | 10.3 | 11.7 | 13.5 | 13.0 |

EXAMPLES 1-2 AND CONTROLS 1-3

A series of dental porcelains were made from the charges listed in Table I (in grams), with the resultant oxide contents listed in Table II.

TABLE I

| Component | Control 2 | Control 3 | Example 1 | Example 2 |
|---|---|---|---|---|
| Nephelene Syenite | 289 | 238.3 | 187.3 | 136.2 |
| $SiO_2$ | 152.6 | 183 | 214 | 245 |
| $Al_2O_3$ | 7.1 | 18.9 | 30.8 | 42.7 |
| $K_2CO_3$ | 54.5 | 64.6 | 75.4 | 86.2 |
| $Li_2CO_3$ | 15.5 | 15.5 | 15.5 | 15.5 |
| $CaCO_3$ | 7.9 | 7.9 | 7.9 | 7.9 |
| MgO | 8 | 8 | 8 | 8 |

The components were blended, ball milled for two hours, transferred to a platinum crucible and heated to 1300° C. (at a heat-up rate of 250° C. per hour) and maintained at that temperature for 3 hours. The material was then quenched in water and reheated to 1000° C. and kept there for 1 hour, after which it was quenched in water. The material was reheated to 1000° C. and kept there for 4 hours, and then quenched in water. The materials were then crushed and ball milled so that they passed through a 165 mesh nylon screen.

Coefficient of thermal expansion test specimens were made by the following procedures:

The thermal expansion test bars were made by pressing 5 grams of powder into a bar ¼×¼×2¼ inches in dimension, and then firing to a temperature of 1800° F. The firing rate was 90° to 100° F. per minute.

In order to evaluate the stability of the ceramic, the thermal expansion test bars were then subjected to 10 heating cycles. Cycles 1, 4, 7, and 10 were heated at a 5° C. per minute heat-up rate to 575° C., and the others

What is claimed is:

1. A single-frit porcelain powder, suitable for use as a porcelain layer on metal-base dental restorations, and having a fired coefficient of thermal expansion within the range of from about 12 to about $14\times10^{-6}$ in/in °C., wherein said single frit porcelain is of the following composition:

| Component | Weight Percent |
|---|---|
| $SiO_2$ | 65¼ ± 4 |
| $Al_2O_3$ | 15 ± 2 |
| $K_2O$ | 12¼ − 1, + 2 |
| Flux | 4 ± 1 |
| MO | 2 ± 1 | wherein M represents calcium, magnesium, or a mixture thereof, and Flux represents sodium oxide or lithium oxide or a mixture thereof, optionally with boron oxide.

2. The porcelain powder of claim 1 wherein the procelain powder has the following composition:

| Component | Weight Percent |
|---|---|
| $SiO_2$ | 65¼ ± 1 |
| $Al_2O_3$ | 15 ± 1 |
| $K_2O$ | 12 ± 1 |
| Flux | 4 ± 1 |
| MO | 2 ± ½ | wherein Flux and M are as defined in claim 1.

3. The porcelain powder of claim 2 wherein the Flux contains 2⅜±⅜ weight percent sodium oxide and 1¼±¼ weight percent lithium oxide, percentages being based upon weight of porcelain.

* * * * *